United States Patent [19]

Lalin

[11] 4,432,248
[45] Feb. 21, 1984

[54] FLUID SAMPLING

[75] Inventor: Hill S. Lalin, Wayne, N.J.

[73] Assignee: Gilian Instrument Corporation, Wayne, N.J.

[21] Appl. No.: 201,823

[22] Filed: Oct. 29, 1980

[51] Int. Cl.³ .............................................. G01N 1/24
[52] U.S. Cl. .............................. 73/863.03; 73/863.23; 73/864.34
[58] Field of Search ............... 55/274, 270; 73/863.01, 73/863.02, 863.03, 863.21, 863.23, 863.24, 863.25; 417/44, 307, 309, 311

[56] References Cited

U.S. PATENT DOCUMENTS

| | | | |
|---|---|---|---|
| 2,942,550 | 6/1960 | Carter | 417/307 |
| 3,295,359 | 1/1967 | Peck | 73/28 |
| 3,501,899 | 3/1970 | Allen | 55/270 |
| 3,677,065 | 7/1972 | Davis | 73/28 |
| 3,803,810 | 4/1974 | Rosenberg | 55/274 |
| 3,855,515 | 12/1974 | Hutchins, Jr. | 417/44 |
| 3,936,237 | 2/1976 | Chattopadyay | 417/311 |
| 3,965,747 | 6/1976 | McCorkle | 73/863.01 |
| 3,976,457 | 8/1976 | Martin | 55/270 |
| 4,140,436 | 2/1979 | Schumacher et al. | 417/311 |
| 4,269,059 | 5/1981 | Baker | 73/863.03 |

FOREIGN PATENT DOCUMENTS 388529 6/1928 France .................................. 55/274

Primary Examiner—S. Clement Swisher
Attorney, Agent, or Firm—Hymen Diamond

[57] ABSTRACT

An air sampler constructed as an integrated unit which can be attached to the clothing of personnel operating in an area where the air must be sampled. The sampler includes a pump, a damper, a regulator, a filter for removing dust or dirt from the air being sampled, and collecting or processing means for the sampled air. The pump is driven by a motor provided with a control which maintains the flow of air through the sampler constant. The regulator is connected directly between the inlet and the outlet of the sampler. It includes a pair of chambers separated by a flexible diaphragm, one chamber connected to the outlet and the other to the inlet. For a pressure differential exceeding a predetermined magnitude between the outlet chamber and the inlet chamber, the diaphragm by its flexing opens a valve to permit air to flow from the outlet to the inlet. The filter is in a transparent container so that it can be seen and removed when it becomes excessively loaded with dirt. The outlet from the filter downstream is near its top so that moisture is prevented from flowing into the air channel downstream from the filter.

14 Claims, 10 Drawing Figures

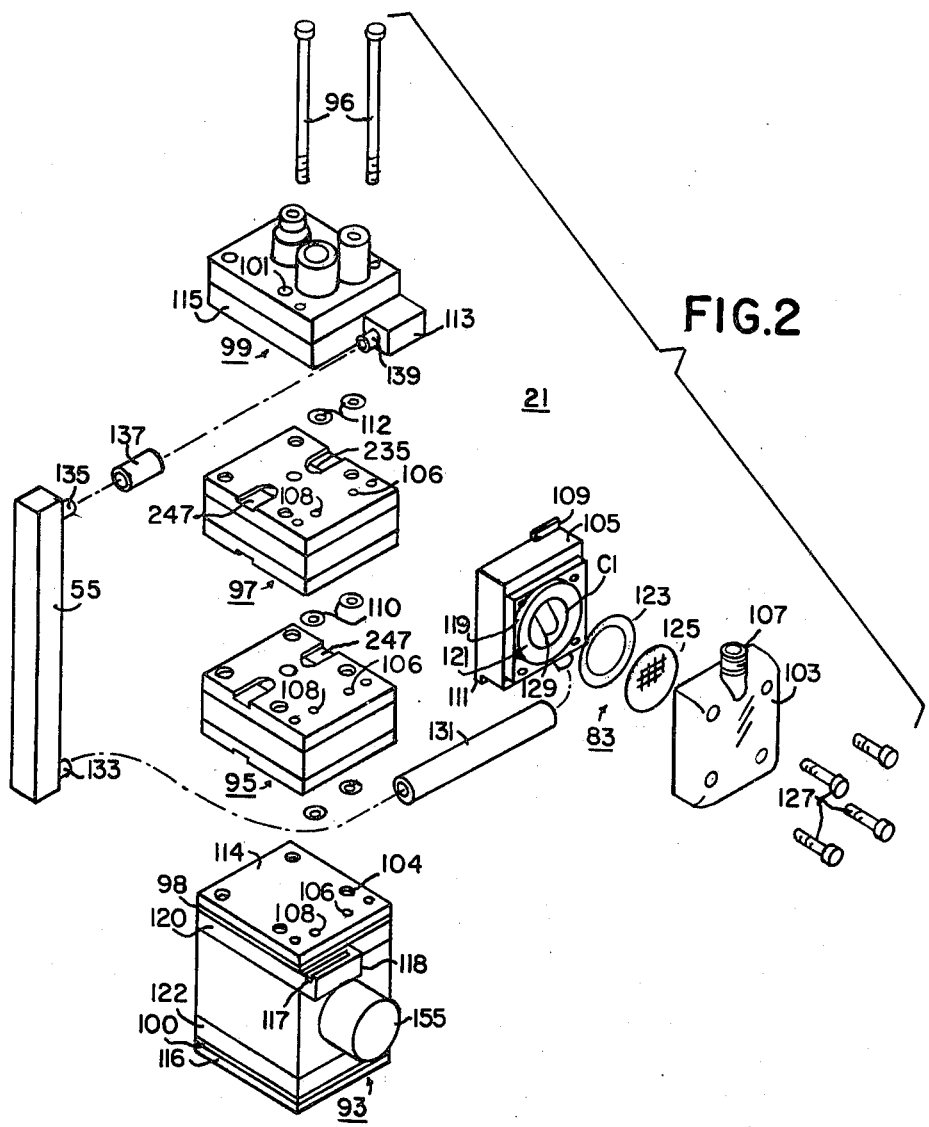

FLUID SAMPLING

BACKGROUND OF THE INVENTION

This invention relates to fluid sampling and has particular relationship to the sampling of gases, predominately air, for selected components. Typically, the fluid sampling with which this invention concerns itself is the sampling of air in plants for harmful components pursuant to the Occupational Safety and Health Act (OSHA) or the sampling of the air at a site such as Love Canal contaminated by chemical waste. Sampling of this type is typically carried out by a sampler carried or "worn by" the person subjected to the harmful components in the air. The sampling may be carried out throughout the working day of the personnel involved or during measured intervals. On occasion, it is also desireable that the flow of air through the sampler be limited.

A sampler includes a pump which pumps the air through a channel including the collecting or processing device which collects and/or measures the concentration of the harmful components. The processing device is usually interposed in the inlet (suction side) to the pump; it may also be in the outlet (pressure side) particularly in the case of bag collection of chemicals. The components sampled are gases or vapors or solid particulate. The air sampled contains dirt such as dust and other debris and it is necessary that such dirt be filtered out prior to entering the pump. The pump is protected by a so-called pump filter through which the pumped air flows as it is drawn into the channel. The function of the pump filter is to protect the pump from this dirt and debris. The filter becomes loaded with dirt during operation and presents an increasing pressure increment to the pump. In addition, there is an increasing impedance to the flow of pumped air through the channel and the flow or the time rate of the flow of air decreases unless the effect of the filter on the flow is compensated. It is necessary that the filter be replaced timely to preclude improper operation. The flow may also vary for other reasons than accumulation of dirt on the filter. In accordance with the teachings of the prior art, a differential pressure switch is interposed in the outlet of the flow channel to suppress the variation in the air flow. This pressure switch responds to the differential between the pressure in a chamber and the pressure outside of the chamber. The chamber is connected to the region outside through a needle valve. The pressure switch opens and closes repeatedly responsive to the pulsations produced by the pumping. One disadvantage of this expedient is that the repeated operation of the pressure switch has a tendency to cause fatigue in its linkages. Another, and more important, disadvantage is that traces of contaminents such as dirt clog or impede the operation of the needle valve precluding satisfactory, stable and reliable response of the switch to pressure variations in the flow channel. Another drawback is that additional pumping power is required to maintain the pressure required for sensing because an increment of pressure is absorbed for maintaining the control power.

It is an object of this invention to overcome the disadvantages of the prior art and to provide a fluid sampler which shall not include moving parts subject to fatigue and which shall operate reliably and with stability to maintain the flow of fluid being sampled substantially constant.

In the practice of the sampling art, it is desireable to vary selectably the flow; i.e., the number of milliliters per second of fluid, which flow through the sampler, specifically through the collecting or processing device. It is an object of this invention to provide a sampler which, (A) shall have the facility of sampling fluid flowing through the collecting device at selectably preset precise rates and (B) shall maintain the preset flow over a wide range of back pressure.

In prior-art practice, the pump filter was not readily accessible or visible. During the use of such a sampler, the pump filter would ultimately become clogged materially deteriorating the operation of the sampler and its reliability. In addition, the pump filter would cease to perform its filtering function and dirt would accumulate in the pump and handicap the operation of the valves. It would then become necessary to dismantle the sampler completely, clean the pump and replace the pump filter. It is an object of this invention to overcome this disadvantage of the prior art and to provide a sampler in which the state of the pump filter shall be readily observable and the filter shall be readily accessible for replacement. It is also an object of this invention to provide a sampler in which the entraining of moisture by the sampled fluid shall be precluded.

SUMMARY OF THE INVENTION

An aspect of this invention arises from the realization that variation in the flow through the sampler varies the pressure differential; i.e., the difference in pressure between the outlet from and the inlet to the pump, which is herein referred to as $\Delta P$, varies the loading on the motor which drives the pump. In accordance with this invention, the motor is controlled responsive to its loading; i.e., to $\Delta P$ in such manner as to maintain the flow through the sampler substantially constant over its operating range of flow.

In accordance with another aspect of this invention, the sampler is provided with a regulator which is integrated into its structure and which is directly interposed between the inlet and the outlet of the sampler. The regulator operates to circulate the quantity of fluid exceeding the selected flow through the pump. Only the selected flow enters the inlet and passes out through the outlet.

In accordance with another aspect of this invention, a filter assembly is provided in which the filter is in a container having at least a transparent outer wall upstream of the filter. The state of the filter can be observed through this wall. This wall is sealed to the remainder of the container but is readily removeable so that the filter is accessible. The connection in the filter assembly to the flow channel opens near the top of the container. Moisture in the gas is deposited in the bottom of the container.

Specifically, the sampler according to this invention is a pneumatic mechanical unit which includes: a pump, a damper assembly, a regulator, a filter assembly and a flow indicator.

The pump is of the preloaded valving type disclosed in application Ser. No. 855,998 filed Nov. 30, 1977 to Hill S. Lalin for *Control for Fluid Flow* and assigned to Gilian Instrument Corp. and now abandoned. The Lalin application is incorporated herein by reference. The pump disclosed in Lalin application is single acting, while the pump included in the sampler according to this invention, disclosed in this application, is double acting. The pump is driven by a DC motor whose speed is controlled.

The damper assembly or damper includes a compression spring sandwiched between two silicon diaphragms, a housing, and necessary seals to allow stacking the damper directly above the pump with the intake air port connecting the damper to the pump intake. A through hole passage is provided in the damper body to allow communicating the pump discharge to the pressure regulator stacked above. A second damper can be mounted above the first for improved damping if required.

The regulator includes a cooperative sensing diaphragm, spring and valve enclosed in a plastic housing which mounts directly to the top of the damper assembly and communicates the inlet and outlet of the regulator to the suction and discharge of the pump respectively. Provisions for shutting off the suction side of the regulator are included. The regulator allows the pump to maintain either the suction or the discharge at a nominal 20" of water.

The filter assembly includes a transparent or see-through housing with air intake boss mounted on the outside of the case. The front housing secures the filter membrane and sealing "O" ring to the rear housing (mounted within the case) by means of four screws thereby providing an airtight seal for the air passage. The rear housing employs a vertical standpipe for conducting fluid into the fluid channel of the pneumatic system. The transparent housing allows visual monitoring of the filter condition as well as of the water carryover into the filter housing. In other words, the transparent housing enables the operator to view the pump filter and to determine when changing is necessary. The standpipe within the rear housing prevents water from directly entering the pump. The standpipe is essentially in a gas reservoir and cooperates with this reservoir to trap moisture before it enters the pump. Moisture might damage the pump.

The flow indicator includes a rotometer vertically mounted in the outside corner of the case and is used to set and indicate pump flows over the operating range, typically between 500 milliliters and 4 liters.

The sampler has an electronic solid-state control which includes a flow compensation control, a battery check, a battery low-voltage indicator, a low-flow indicator, a timer and an on-off switch.

The flow compensation control provides for constant air flow from the pump at any preset flow over range of operation of the sampler, typically between 500 milliliters and 4 liters per minute. The compensation control is effective because of the linearity of the pump incorporating the pre-loaded valving disclosed in Lalin Application. The compensation control includes a sensing resistor mounted in the motor leg which provides a voltage signal proportional to the motor load current to the power supply which in turn adjusts the motor voltage proportionately to the pump-load line curves thereby maintaining relatively constant flow over a back pressure range typically from 0 to 40 inches of water (positive or negative) at flow rates over the operating range. Additional features are automatic pump shutdown and fault indication should the pump be restricted (suction or discharge) beyond its operating range.

A visual battery check indicator is provided which is activated by a press-to-test switch which senses the overcharge state of the batteries. The batteries are typically NICAD. There is a visual indication as to the battery capacity to run a minimum eight hour sample at any flow regime within the instrument's capability.

A visual low battery indicator is provided which is enabled should the voltage to the electronics control fall below the minimum overhead voltage required to properly operate the instrument. At the same time that this indicator is enabled, the pump and timer are stopped and the indicator is latched on. The timer is stopped showing the number of hours of operation prior to the fault.

The low-flow indicator senses an out of flow condition and stops the pump and timer and enables the indicator after a suitable time delay which is a function of the overload condition.

A presettable electronic timer and display is provided which indicates the number of hours of operation and which can be preset in 10 minute timing intervals typically up to 990 minutes (16.5 hours) to stop the pump. Timing is set by means of two 10-position switches, the first providing 10 minute intervals, the second 100 minute intervals. The display is blanked until the press-to-test button is activated. The clock which controls the timer automatically stops when actuated by any of the above fault conditions (out of spec flow, low battery, etc.). This feature allows the user to always achieve a valid sample even if the total sampling period is not realized.

The on-off switch upon application of power resets the counter to 0, enters the programmed time into the counter for automatic shutdown, and simultaneously resets all error latches to the no fault condition.

At this point it appears desirable to describe the function of the regulator. The sampler can operate either at full normal flow of the fluid under observation or at low flow. The regulator enables stable operation of the sampler in the low-flow setting. As stated, the regulator is integrated into the sampler and is interposed between its inlet and outlet; i.e., between the pump suction and pump discharge ports.

The regulator when set at a pressure differential, for example, at 20" of water in conjunction with calibrated orifices at the inlet or outlet of the sampler, allows the sampler to provide for constant flow multi-tube sampling. The flow across an orifice is a function of the pressure differential across the orifice. Consequently, an orifice can be designed to provide the desired flow range if the pressure drop across the orifice is set to the pressure drop for which the orifice is calibrated.

In operation the pump flow is set typically to 1 liter per minute flow and a selected restrictor orifice is inserted between the collecting device (singly or manifolded) and the pump inlet side. The pump sucks the intake side down to 20" of water (negative) which causes the pressure regulator valve to open to make up the flow difference from the pump discharge air. For example: If a 200 cc orifice is inserted between the sampling tube and the inlet side of the pump, 200 cc passes through the orifice and 800 cc of make up air is supplied from the pump discharge side through the regulator and back into the pump for an equivalent of 1 lpm. The same concept is applicable to the discharge side, a restrictor orifice can be placed between the pump discharge port and the fluid collecting device (bag sampling). In this operating mode, the pump pushes the discharge side up to 20" of water (positive) which causes the pressure regulator valve to open bypassing the flow difference to the pump inlet.

BRIEF DESCRIPTION OF THE DRAWINGS

For a better understanding of this invention, both as to its organization and as to its method of operation, together with additional objects and advantages thereof, reference is made to the following description, taken in connection with the accompanying drawings, in which:

FIG. 2 is an exploded view in isometric of the pneumatic assembly of the apparatus shown in FIG. 1;

FIGS. 7 and 8 show the magnitudes and types of the components incorporated in an embodiment of this invention which operates satisfactorily. This data is included in FIGS. 7 and 8 for the purpose of aiding those skilled in the art in practicing this invention, as required 35 USC 112, and not with any intention of any way limiting this invention.

DETAILED DESCRIPTION OF EMBODIMENT

Figure 1:
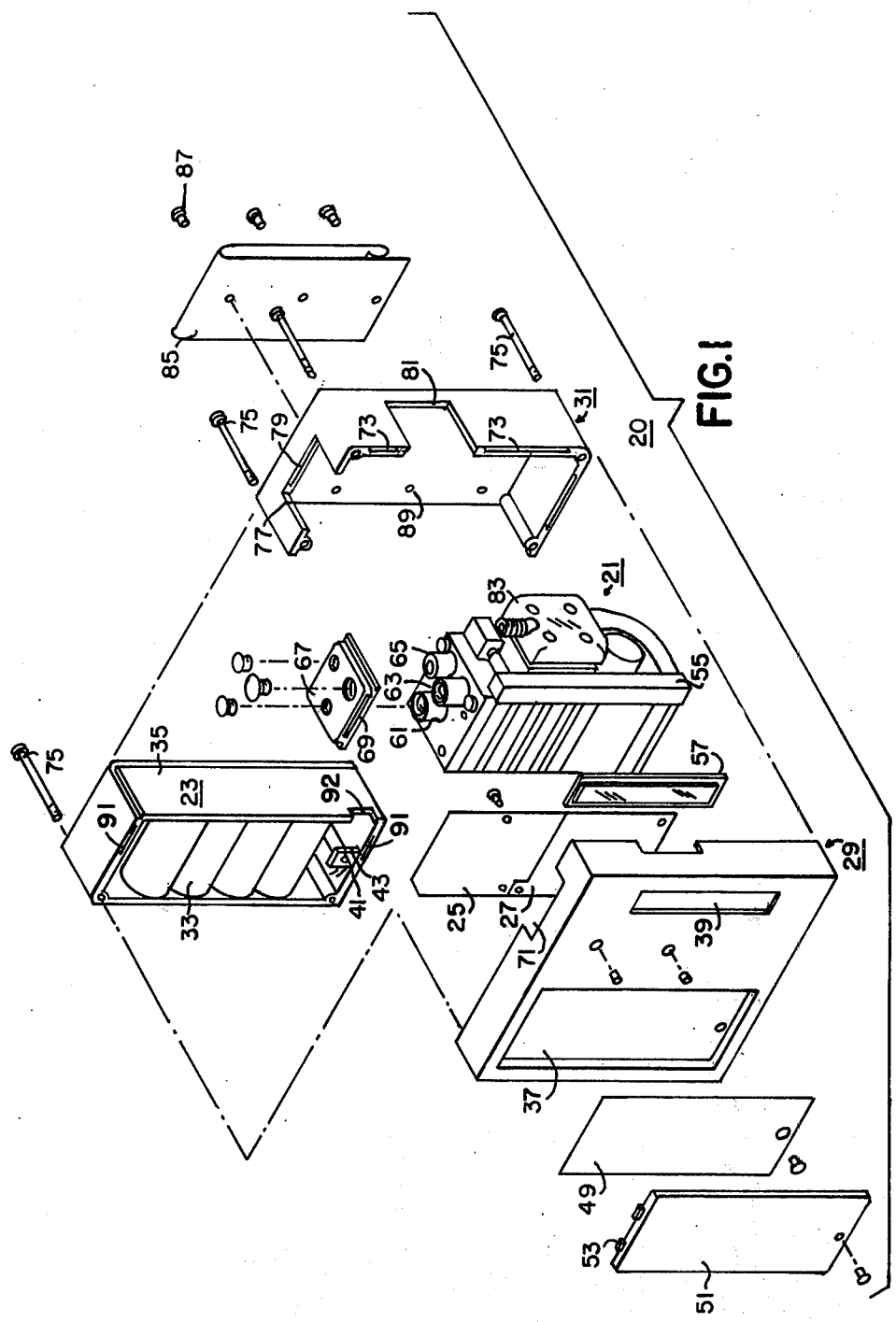
FIG. 1 is an exploded view in isometric of an embodiment of this invention.
Figure 1A:
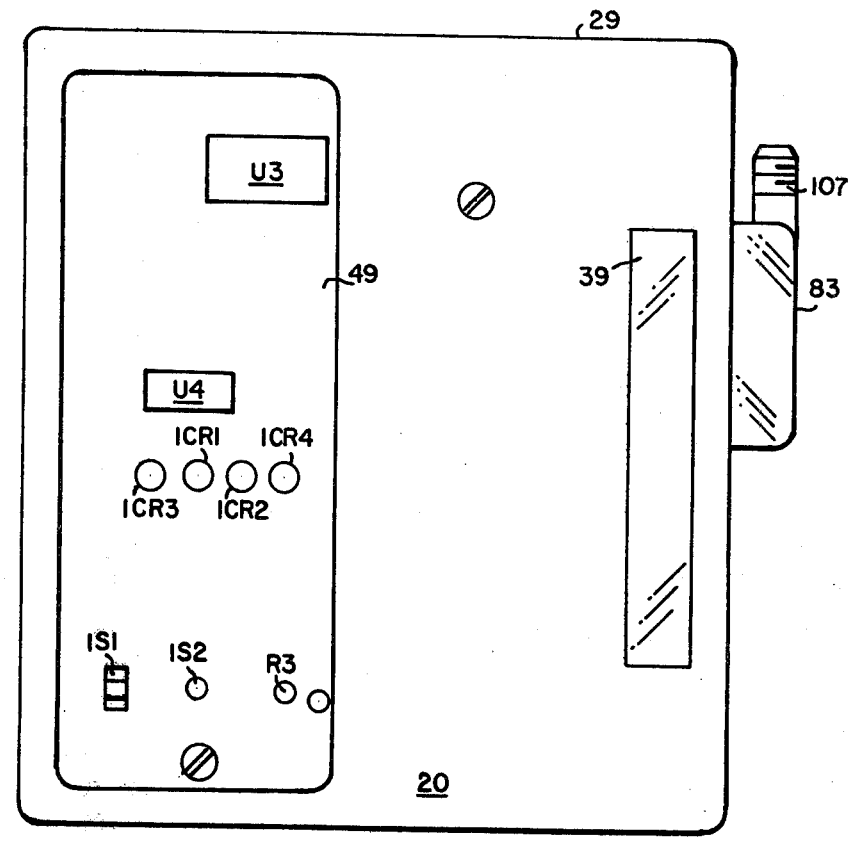
FIG. 1A is a view in front elevation of this embodiment with the cover over the name plate removed.

The apparatus shown in the drawings is a sampler 20 including a pneumatic assembly 21 (FIG. 2), a battery pack 23, a board 25 containing the timing network (FIG. 7) on a printed circuit and a board 27 containing the control network (FIG. 8) on a printed circuit. The sampler 20 has a casing including a front case 29 and a rear case 31. The battery pack 23 is a cartridge including a battery 33 in a container 35. The front case 29 is open at its left-hand end (with reference to FIG. 1) and includes a frame-like recess 37 on the left (with reference to FIG. 1) and a slot 39 on the right. The timing-network board 25 and the control-network board 27, include conductors that are interconnected (FIGS. 7 and 8) and are coextensive vertically (with reference to FIG. 1). The planar unit formed by the boards 25, 27 is on bosses (not shown) extending from the back of recess 37. The battery pack 23 is mounted behind the boards 25 and 27 with the battery 33 contiguous to the boards and the socket receptacles 41 and 43 of the battery connected to terminals or pins 45 and 47 (FIG. 8) of the control network 27. A nameplate 49 is mounted in the recess 37 abutting the recess. A cover 51 extends into the recess 37 flush with the outer rim of the front case 29 and abuts the name plate 49. The cover 51 has tongues 53 which engage cooperative grooves (not shown) in the top of recess 37.

The penumatic assembly 21 is supported in the right-hand compartment (with reference to FIG. 1) of the front case 29. A flowmeter 55 in the pneumatic assembly 21 is disposed oppositely the slot 39. A window 57 extends into the slot 39 between the flowmeter 55 and the slot with its offset frame abutting the boundaries of the slot 39.

The top of the pneumatic assembly 21 has hollow bosses 61, 63, 65. An insert 67 is disposed on the top extending over the bosses 61-65. The insert 67 has a tongue 69 which engages a groove (not shown) in the edge of a slot 71 in the top of the front case. The rear case 31 encompasses the pneumatic assembly 21, its inner edge engaging the inner edge of the front case. The inner edge of the rear case is provided with tongues 73 which engage slots (not shown) in the inner edge of the front case. The rear case 31 is secured by screws 75 through bosses in its four corners to the front case 29. The rear case has a slot 77 in its top in which it engages the insert 67. The inner edge of the slot 77 has a groove 79 which is interlocked with a tongue (not shown) in the insert 67. In its side the rear case has a slot 81 which encompasses the inner boundary of the pump filter assembly 83.

A belt clip 85 is secured by rivets 87 which pass through holes 89 near the left-hand edge of the rear case 31. The belt clip 85 extends over this left-hand edge defining a vertical space or pocket for receiving the battery pack 23.

In assembling the sampler 20, the pneumatic assembly 21 is first enclosed between the right-hand compartment of the front case 29 and the rear case 31 with the rear case 31 secured to the front case 29 and the window 57 in the slot 39. The belt clip 85 is secured to the left end of rear case 31 providing a pocket or slot between the clip 85 and the left-hand side of front case 29. The planar unit composed of the boards 25 and 27 is secured to the bosses (not shown) on the back of the recess 37. The battery pack 23 is slid through the left-hand open end of the front case 29 into the pocket between the back of the front case 29 and the belt clip 85. Tongues 91 in the upper and lower ends of the battery container 35 engage grooves (not shown) in the rear of the front case 29. The battery pack is slid along the flat circuit unit 25-27 so that the pins 45 and 47 (FIG. 8) enter the sockets 41 and 43 and are fully plugged in in the final position of the battery pack 23. The step 92 in the base of the container 35 of the battery pack 23 is dovetailed with a projection (not shown) in the base of the pneumatic assembly 21.

Outside dimensions of a typical sampler according to this invention areas follows: Length (measured horizontally along the plane of the drawing with reference to FIG. 1) $4\frac{5}{8}''$, depth (into plane of drawing FIG. 1) 1 5/16", heighth (vertically in FIG. 1) 5". The overall length includes $\frac{1}{2}''$ for the filter 83; the overall depth includes $\frac{1}{4}''$ for the belt clip 85.

Figure 3:
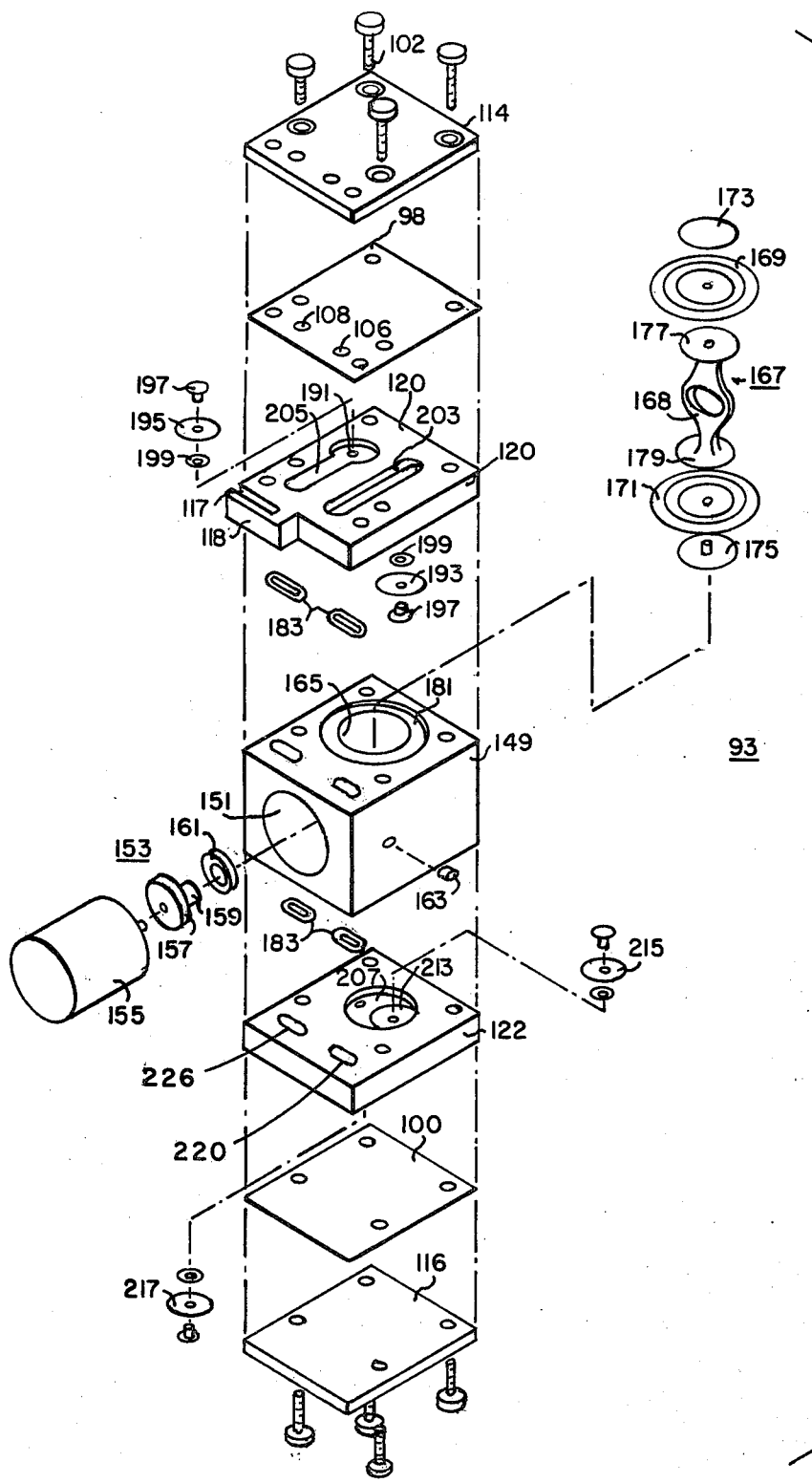
FIG. 3 is an exploded view in isometric showing the pump incorporated in the embodiment of this invention shown in FIG. 1.
Figure 4:
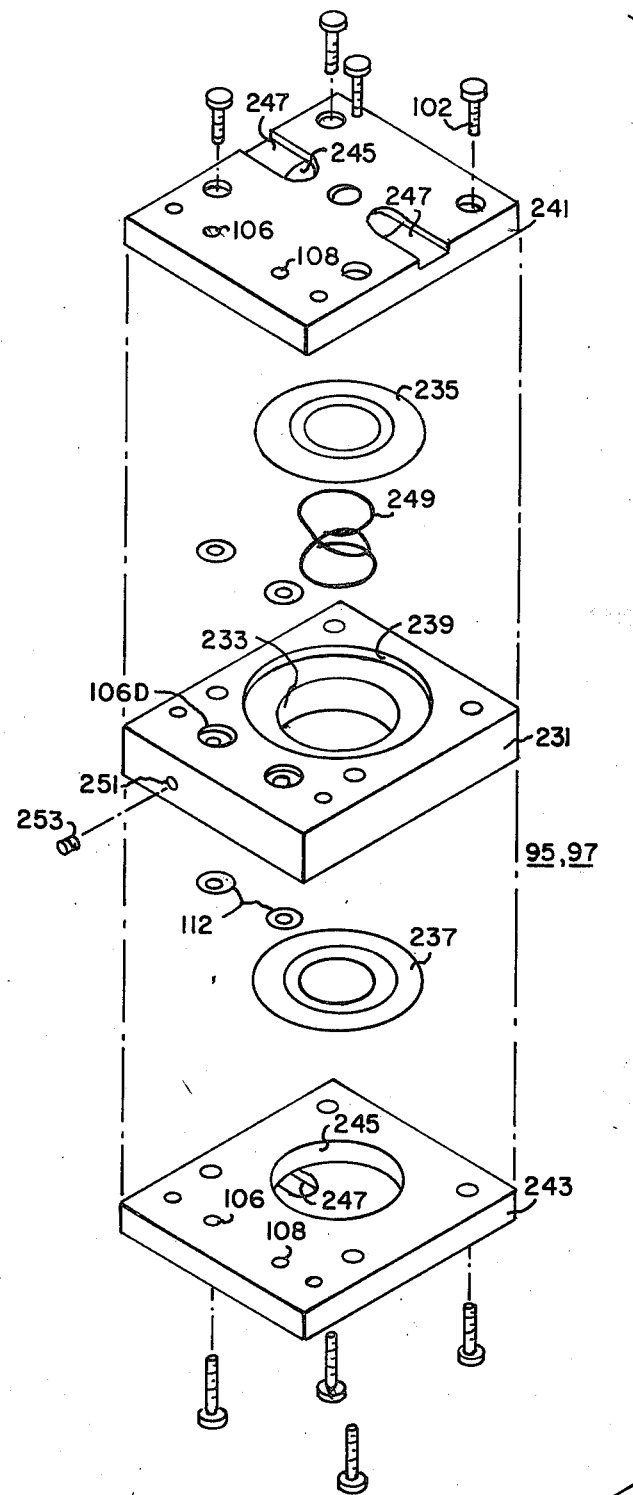
FIG. 4 is an exploded view in isometric showing the damper incorporated in the embodiment of this invention shown in FIG. 1.
Figure 5:
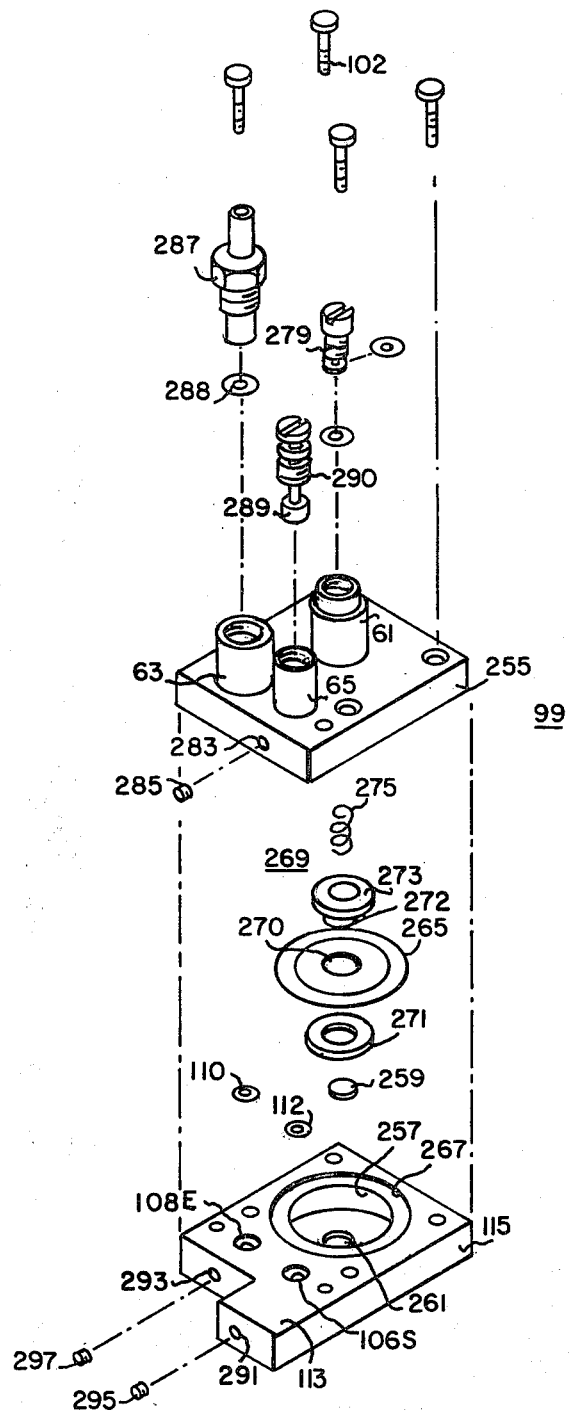
FIG. 5 is an exploded view in isometric showing the regulator incorporated in the embodiment of this invention.
Figure 6:
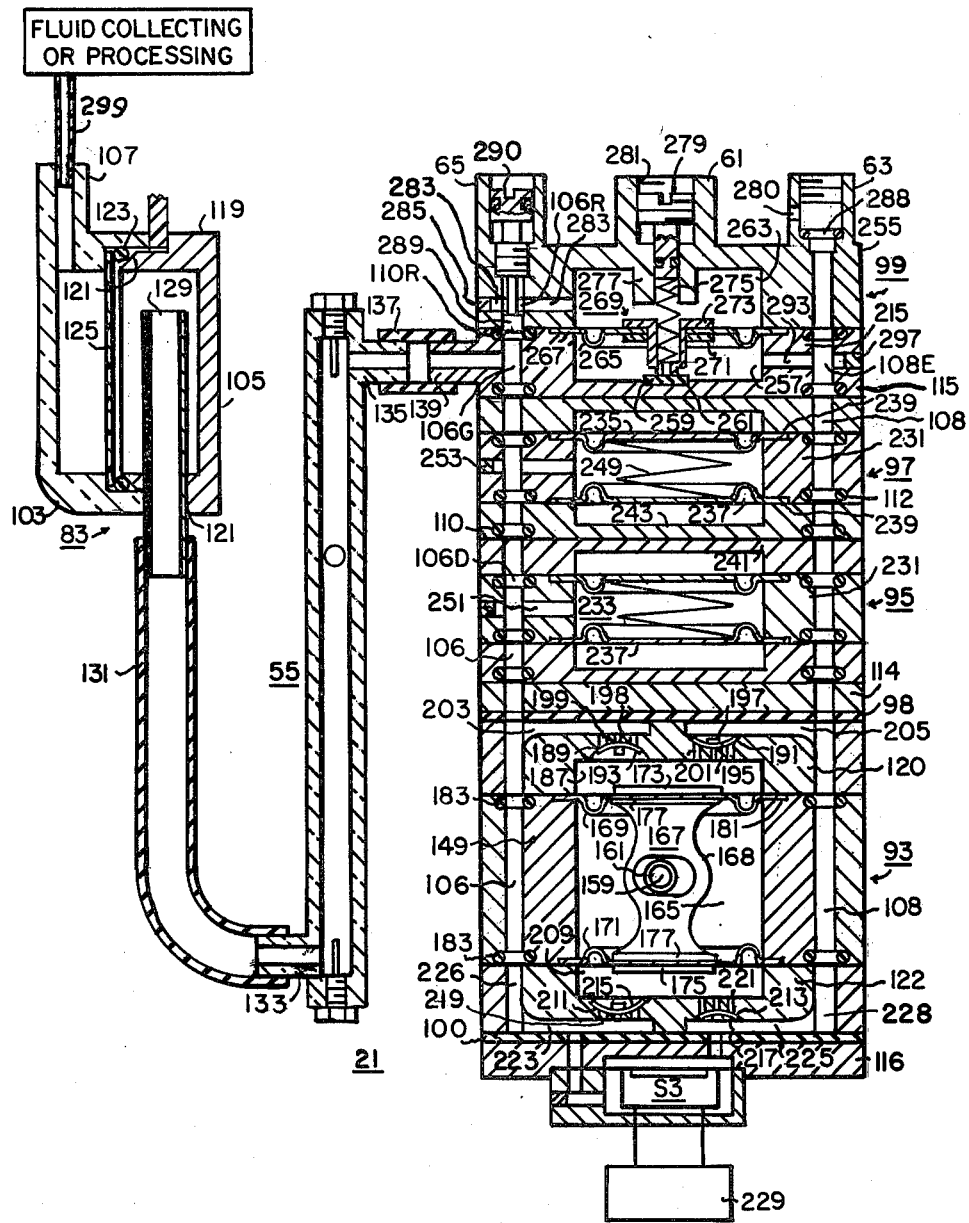
FIG. 6 is a view in longitudinal section, partly diagrammatic, of the pneumatic assembly with the section planes displaced transversely with reference to each other to facilitate the understanding of this invention.

The pneumatic assembly 21 (FIG. 2) includes in addition to the flowmeter (ROTOMETER) 55 and the pump filter 83, the pump assembly 93, damper assemblies 95 and 97 and regulator 99. The pump 93, dampers 95 and 97, and regulator are stacked and secured together by screws 96 through holes 101. In the stack are included gaskets 98 and 100 between the top plate 114 and the upper valve plate 120 and between the bottom plate 116 and the lower valve plate 122 of the pump assembly 93. Each assembly 93, 95, 97, 99 is held together by screws 102 (FIGS. 3, 4, 5) countersunk in holes 104. The pump 93 and the dampers 95 and 97 and regulator 99 have coextensive openings which, when these components are stacked, form a suction channel 106 (FIG. 6) through which air is sucked into the pneumatic assembly 21 by the pump. The components 93, 95, 97 and 99 also have openings which form the exhaust channel 108 through which air is exhausted from the pneumatic assembly when these components are stacked. As shown in FIG. 6, the channel 106 is coaxial with boss 65 and the channel 108 with boss 63. The openings in the pump, dampers, and regulator which form channels 106 and 108 are sealed by O-rings 110 and 112 compressed between each pair of abutting components 93 and 95, 95 and 97, and 97 and 99.

Figure 2A:
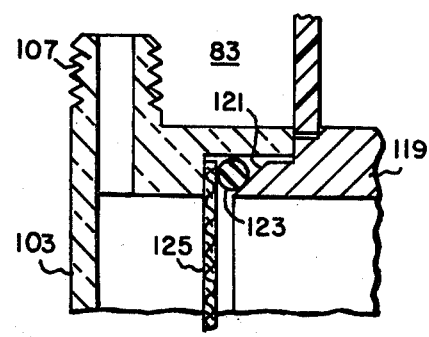
FIG. 2A is a fragmental view in longitudinal section showing the transparent pump-filter housing of the apparatus shown in FIGS. 1 and 1A and its associated components.

The filter assembly 83 is best shown in FIG. 2. It includes a casing formed of a front housing 103 and a rear housing 105. At least the front housing 103 is transparent and has fitting 107 for receiving the fluid. The rear housing 105 has an upper tongue 109 and a lower tongue 111. The upper tongue 109 engages a slot (not shown) in a projection 113 extending from the lower plate 115 of the regulator 99 through which air is sucked by the pump through the pneumatic assembly 21. The lower tongue engages a groove 117 in a projection 118 of the upper valve plate 120 of the pump 93. In this way, the filter assembly 83 is suspended from the body of the pneumatic assembly. From the surface of the rear housing 105 facing the front housing 103 an annular projection 119 extends. The outer surface 121 of the projection 119 is beveled inwardly at an angle of about 45°. Between the beveled surface 121 of the annulus 119 and a recess (not shown) in the front housing an O-ring 123 and a filter 125 are interposed (FIG. 2A). When the housings 103 and 105 are secured together by screws 127, the O-ring 123 is compressed between the beveled surface 121 and the rim of the recess (not shown) sealing the chambers defined between the filter 125 and the recess on one side and between the filter and the rear housing on the opposite side. The fitting 107 communicates with the recess thus transmitting the sucked-in air through the filter 125. The filter 125 is clearly visible through the front housing 103.

An exit tube 129 is sealed through the lower wall of the rear housing 105. This tube passes through the annulus 119 and opens near the top of the rear housing 105 within the annulus. Air passing through the filter 125 must be pushed to the top of the chamber defined by the annulus 119 before it can exit through tube 129. Water droplets or vapor in the air are deposited in the lower region of the chamber. The tube 129 is connected by flexible tubing 131 to inlet 133 of flowmeter 55. The outlet 135 of flowmeter 55 is connected through tubing 137 to inlet 139 in projection 113. Filtered air is thus sucked in through the pneumatic assembly 21.

The pump 93 (FIG. 3) includes a body 149 in the form of a rectangular parallelepiped in addition to the top valve plate 120, the bottom valve plate 122, the top plate 114, the bottom plate 116 and the gaskets 98 and 100. The body 149 has a horizontal cavity 151 into which an eccentric drive 153 extends. This drive includes a motor 155 and an eccentric 157 driven by the motor 155. The eccentric 157 has an eccentrically disposed pin 159 which is rotatable in a bearing 161. The motor 155 is secured in the cavity 151 by a set screw 163.

The body 149 also has a vertical bore 165 which extends through the top and bottom of the body 149 and is in communication with the cavity 151. Within the vertical bore 165, a diaphragm assembly 167 is mounted. This assembly 167 includes a yoke 168, upper and lower diaphragms 169 and 171 and diaphragm retainers 173 and 175. The diaphragms 169 and 171 are held in engagement with end plates 177 and 179 of the yoke 168 by the retainers 173 and 175. The diaphragms 169 and 171 are seated in annular recesses 181 (FIG. 3) in the top and bottom of the body 149. They are secured in these recesses by the top plate 120 and the bottom plate 122. The pin 159 and bearing 161 extend into the opening in the yoke 168 with bearing 161 engaging the surface bounding the opening. As the pin is rotated by motor 155, the yoke 168 is moved upwardly and downwardly correspondingly flexing diaphragms 169 and 171 upwardly and downwardly in opposite phase. There are O-ring seals 183 (FIGS. 3, 6) between the body 149 and the upper and lower valve plates 120 and 122 which seal the bore 165.

The upper valve plate 120 has a circular opening opposite to and sealed by the diaphragm 169. The diaphragm 169 and the upper valve plate 120 at the opening form a plenum 187 (FIG. 6). The base of this plenum in the upper valve plate has disk shaped cavities or valve-seats 189 and 191 (FIG. 6). In each cavity, a prestressed valve plate 193 and 195 (best seen in FIG. 6) is seated. Each valve plate is secured in the cavity and pre-stressed by a retainer 197 which engages a spacer 198 on the opposite side of the valve plate. There are holes 199 and 201 in the seats 189 and 191; hole 199 connecting the plenum 187 to the suction channel 106 and hole 201 connecting the plenum to the exhaust channel 108. This connection is through slot 203 and key-shaped slot 205 in the upper valve plate 120. The valve plate 193 is positioned so as to disengage its seat 189 when the diaphragm 169 moves downwardly creating a partial vacuum in plenum 187. For this setting of the diaphragm the other valve plate 195 is urged into tighter engagement with its seat 191. Conversely, when diaphragm 169 is moved upwardly increasing the pressure in plenum 187, valve plate 195 opens and valve plate 193 closes more tightly.

The lower valve plate 122 likewise has a circular hole 207 (FIG. 3) which is sealed by diaphragm 171 to form plenum 209 (FIG. 6). The base of plenum 209 has disk-shaped valve seats 211 and 213 on which valve plates 215 and 217 are seated. The seats have holes 219 and 221 connecting the plenum to suction channel 106 through slot 223 (FIG. 6) and to the exhaust channel 108 through slot 225. The body 149 is connected to the suction channel 106 and the exhaust channel 108 through oval slots 226 and 228 which are sealed by O-rings 183.

A pressure switch S3 (FIGS. 6, 8) is suspended from the bottom plate 116. This switch S3 is in communication with the suction slot 223 on one side and with the exhaust slot 225 on the opposite side and responds both to excessive vacuum on the suction side and to excessive pressure on the exhaust side to actuate a latch 4U3 (FIG. 8) to stop operation under conditions requiring such stopping, for example, when a suction or exhaust line is plugged. The switch S3 acts as back-up for the electrical protective apparatus.

Each damper 95 and 97 (FIG. 4) has a damper body 231. This body has a vertical circular bore 233. Both ends of the bore 233 are closed by flexible diaphragms 235 and 237. The diaphragms are held in engagement at their peripheries with annular recesses 239 in the opposite faces of the body 231 by top plate 241 and bottom plate 243. Each plate 241 and 243 has a circular recess 245 in its inner surface. In its outer surface, the top and bottom plates 241 and 243 each has slots 247 which communicate with the recess 245. The external surface of each diaphragm 235 and 237 is thus under atmospheric pressure. The pressure on the outer surfaces of the diaphragms 235 and 237 is counteracted by a spring 249 which exerts pressure on each of the diaphragms. A hole 251 is drilled through a wall of the body 231 which penetrates through the hole 106D in the body which is in suction channel 106 and through the bore 233. This hole 251 connects suction channel 106 to the cavity formed between the diaphragms 235 and 237 and the bore. The hole 251 is closed externally by a plug 253. As the pump 93 operates, pulses of air are sucked into channel 106. These pulses also flow through hole 251 into the cavity defined by diaphragms 235 and 237 and the bore 233 and reacts with the spring 249 and the diaphragms producing pulses which are out of phase with the pulses flowing into channel 106. The pulses which flow through the channel into the pump plenums 187 and 209 (FIG. 6) are thus smoothed out. The diaphragms 235 and 237 and spring 249 function analogously to an electrical capacitive-inductive filter in parallel with a current load analogous to the plenums.

The regulator 99 (FIG. 5) includes in addition to bottom plate 115, top plate 255. The bottom plate 115 has a cylindrical cavity 257. A pad 259 is disposed in a recess 261 in the base of the cavity 257. The top 255 also has a cylindrical cavity 263 (FIG. 6). A flexible diaphragm 265 is seated with its rim engaging an annular recess 267 bounding the cavity 257. The diaphragm is held between the top plate 255 and the bottom plate 115. A flanged hollow valve member 269 extends through an opening 270 in the center of diaphragm 265. The valve member 269 is secured by a retainer washer 271, the internal rim of the diaphragm being engaged by the flange 273 of the valve member on top and the retainer 271 on the bottom. Externally, the valve member 269 has an attenuated tip 272 which serves as a valve seat. Internally, the valve has a shoulder above the tip. A spring 275 (FIG. 6) engages the shoulder at its lower end and extends into a hollow projection 277 which is coaxial with hollow boss 61 extending from top plate 255 where it engages the end of screw 279. The head of screw 279 is threaded and meshed with an internal thread 281 at the top of hollow boss 61. Screw 279 may be screwed in or out as necessary to compress or relax spring 275. The spring urges the tip or seat of valve member 269 into engagement with pad 259. Hollow boss 65 is coaxial with and in communication with the suction channel 106. Hollow boss 63 of the top plate 255 is coaxial and in communication with the exhaust channel 108. This boss 63 has a lateral hole 280. In operation in which the collector is on the suction side, air passing through the exhaust or pressure channel 108 is exhausted through the lateral hole 280 into the housing for the sampler. The housing is substantially hermetic and the resulting increase in pressure prevents the penetration of debris into the housing. The boss 63 is threaded internally and is capable of receiving fitting 287 (FIG. 5). The inner rim of this fitting engages O-ring 288 (FIGS. 5, 6) to seal the hole 280 against passage of exhaust air. The fitting 287 is used in bag-collector or other like operation where the collector or meter is on exhaust side. The bag (not shown) or the like is connected to receive the exhaust air through the fitting.

A lateral hole 283 (FIG. 6) is drilled through the top plate 255 penetrating the opening 106R of the suction channel in the top plate and extending into cavity 263. This hole 283 is closed by a plug 285. The suction channel 106 is thus connected to cavity 263. A screw 290 (FIG. 5) is provided for blocking the connection between the suction channel 106 and the cavity 263. This screw passes through boss 65 and meshes with an internal thread in top 255. At its lower end, screw 290 has a tip 289 which engages O-ring 110R to block the connection. Lateral holes 293 and 291 (FIGS. 5, 6) are also bored through the body of bottom plate 115 and through the projection 113 and body of plate 115. Hole 291 extends into the suction channel 106 at opening 106S. Hole 293 penetrates the exhaust channel at hole 108E and extends into cavity 257. The holes 291 and 293 are closed by plugs 295 and 297. Hole 291 connects the flowmeter 55 to the suction channel. (FIG. 6 is not accurate on this feature). Instead of being directly connected to hole 291, inlet 139 of the regulator extends into projection 113 (FIG. 5) at right angles to hole 291. Inlet 139 communicates with hole 291. The position of hole 291 is shown in FIG. 5.

In the operation of regulator 99, screw 290 is turned upwardly so that cavity 263 is connected to and is at the same pressure as the suction channel 106. The force of the spring 275 which is exerted to maintain valve 269 closed is counteracted by the differential in pressure between cavity 257, which is connected to and is at the pressure of the exhaust channel, and cavity 263. When the flow of air into the fitting 107 is restricted by an orifice 299, there is a differential in pressure between the atmosphere and the inner end of the orifice 299. In a typical situation, it may be assumed that pump 93 is set to operate at 1 liter per minute and the flow through the orifice is at 200 milliliters per minute. The air in cavity 263 is then exhausted while the pressure in cavity 257 remains at atmospheric pressure. Screw 279 compressed spring 275 so that for the differential in pressure which is produced, valve 269 opens. The exhaust gas is then pumped partly out through boss 63 and partly through the gas circuit including channel 108, hole 293, valve 269, hole 283, suction channel 106 and through the pump. For the differential in pressure between cavity 257 and cavity 263 properly set and for the pump set to pump 1 liter per minute, 200 milliliters perminute flows out through boss 63 and 800 milliliters per minute circulates in the above-described loop.

The pneumatic assembly 21 is controlled electrically by the timer board 25 and the control board 27. Actual networks which operate satisfactorily are shown in the schematics, FIG. 7 for the timer, and FIG. 8 for the control network. In these networks, integrated circuits are to a large extent included. For example, operational amplifiers U1-3U1 are part of a 339 integrated circuit. The parts of the integrated circuits included are not identified. The actual magnitudes of components are also shown. Where the magnitude of a capacitor is shown as a number alone, for example, 0.001 for capacitor C1, FIG. 7, the capacity is in micro-microfarads (piko farads). Magnitudes in micro-farads are so labeled. Resistor magnitudes are in ohms, in thousands of ohms where a number is followed by a "K", in millions of ohms where a number is followed by an "M". To a large extent, input and output signal magnitudes are referred to digitally as 1 or 0, instead of high and low. A 1 is a voltage of 2.4 volts and higher; a 0 is 0.4 volts and lower. However, on occasion, an intermediate state exits at about 2.5 volts at which certain operation is enabled. Output on the control board 27 and inputs to the timer board 25 are labeled T1M, etc. A bar over an input, for example T1M, means that a 0 is impressed to produce the required operation. Where a bar is absent, for example INH, a 1 is impressed to produce the required operation, reset in this case. Since the container of the sampler is composed of an electrical insulator, grounding is provided by conductors on the printed circuit boards 25 and 27. Power grounding is represented conventionally by three lines GR of decreasing length. Digital grounding is represented by a fork-like symbol GRD.

Figure 7:
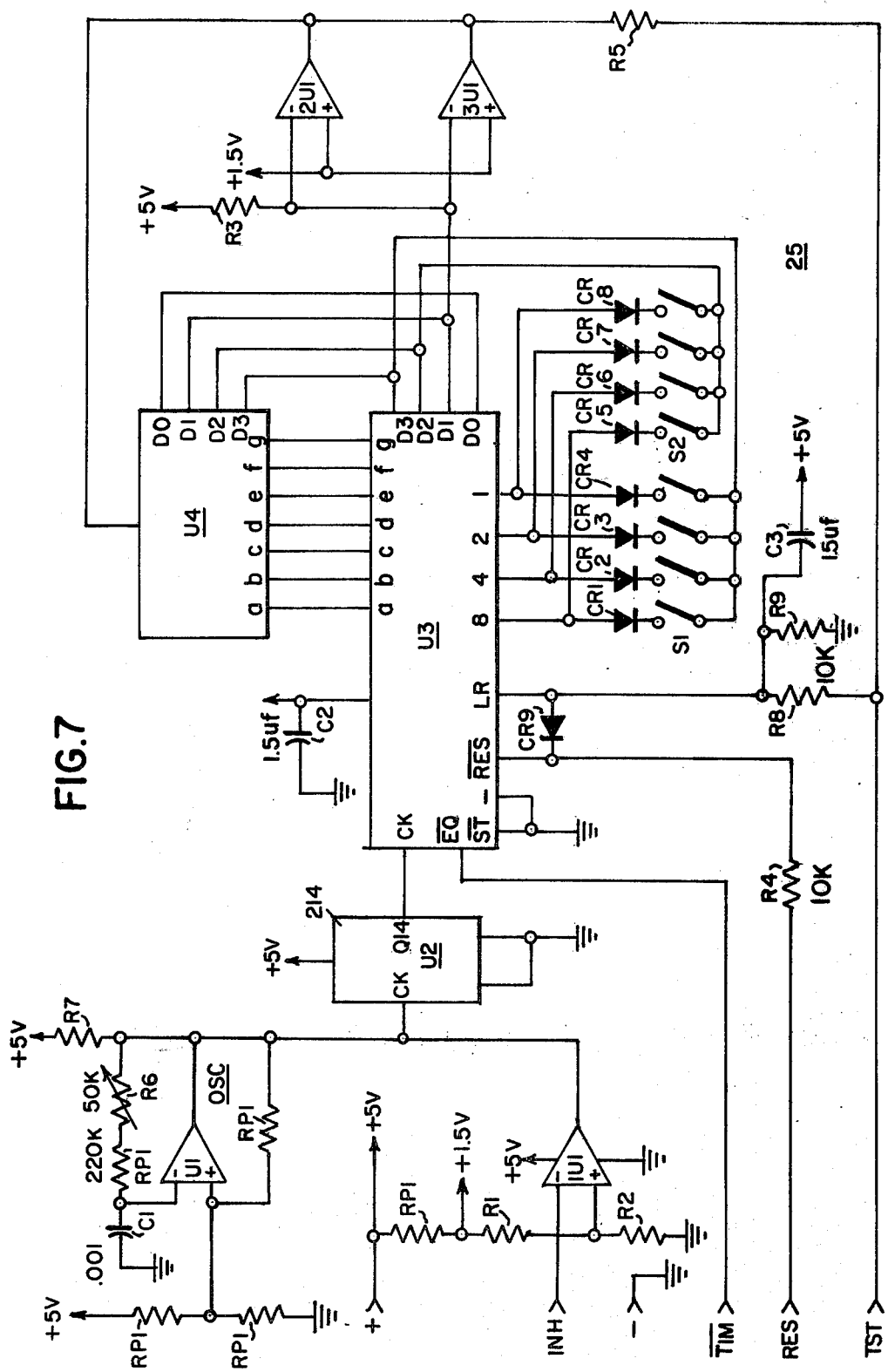
FIG. 7 is a schematic showing the timing network incorporated in this invention.

The apparatus shown in FIG. 7 includes an oscillator OSC, a frequency divider U2, typically 14 stages (divides by $10^{14}$), a counter U3 and a display U4. The oscillator OSC includes the operational amplifier U1, the calibration resistor R6, the resistors RP1 and the capacitor C1. Its period, typically is about 366 microseconds. The output of the oscillator OSC is impressed on the clock input CK of the divider U2. At its output Q14, the divider U2 produces a low frequency signal, typically 1 cycle every 6 seconds. This signal is impressed on the clock input CK of the counter U3. The number of counts which the counter produces is preset by the selector switches S1 and S2. S1 sets the counts in hundreds and S3 in tens. The switches operate through diodes CR1 through CR8. Counter U3 includes a register and a comparator (neither shown).

At the start of an operation when power is first applied, input LR of U3 goes to 1 from the 5 volt supply through capacitor C3. As capacitor C3 charges up, input LR goes to 2.5 volts. Ultimately, capacitor C3 is fully charged and LR becomes 0. When LR goes to 1, the number set by the switches S1 and S2 is loaded in the register of U3. The reset output RES is set to 0 and the counting starts after LR goes to 2.5 volts. The counting continues with LR 2.5 volts or lower. When the comparator finds the input count to be equal to the count stored in the register, EQ goes to 0, latch 1U3 (FIG. 8) is set producing a 1 at INH, inhibit. The output of amplifier 1U1 (pin 13) goes to 0, stopping oscillator OSC to stop the counting. Also the motor 155 is stopped. In each latch such as 1U3 a setting produced by a 0 at S is latched in and remains latched in after the 0 is removed from S until a 0 is impressed on R to reset the latch. With LR 0, the display U4 is blanked. A signal on TST produced by closing switch 1S2 (FIG. 8) enables the display U4. The display is impressed from counter U3 on display U4 through outputs a through g of U3 and inputs a through g of U4. Outputs D0 through D4 of U3 transfers the digits of the display through input D0 through D3 of U4. D3 is the most significant digit and D0 the least significant digit. The decimal point is derived through operational amplifiers 2U1 and 3U1, with TST, test, at 1. When D1 is 1, there is no decimal point. With D1 at 0, there is a decimal point.

Figure 8:
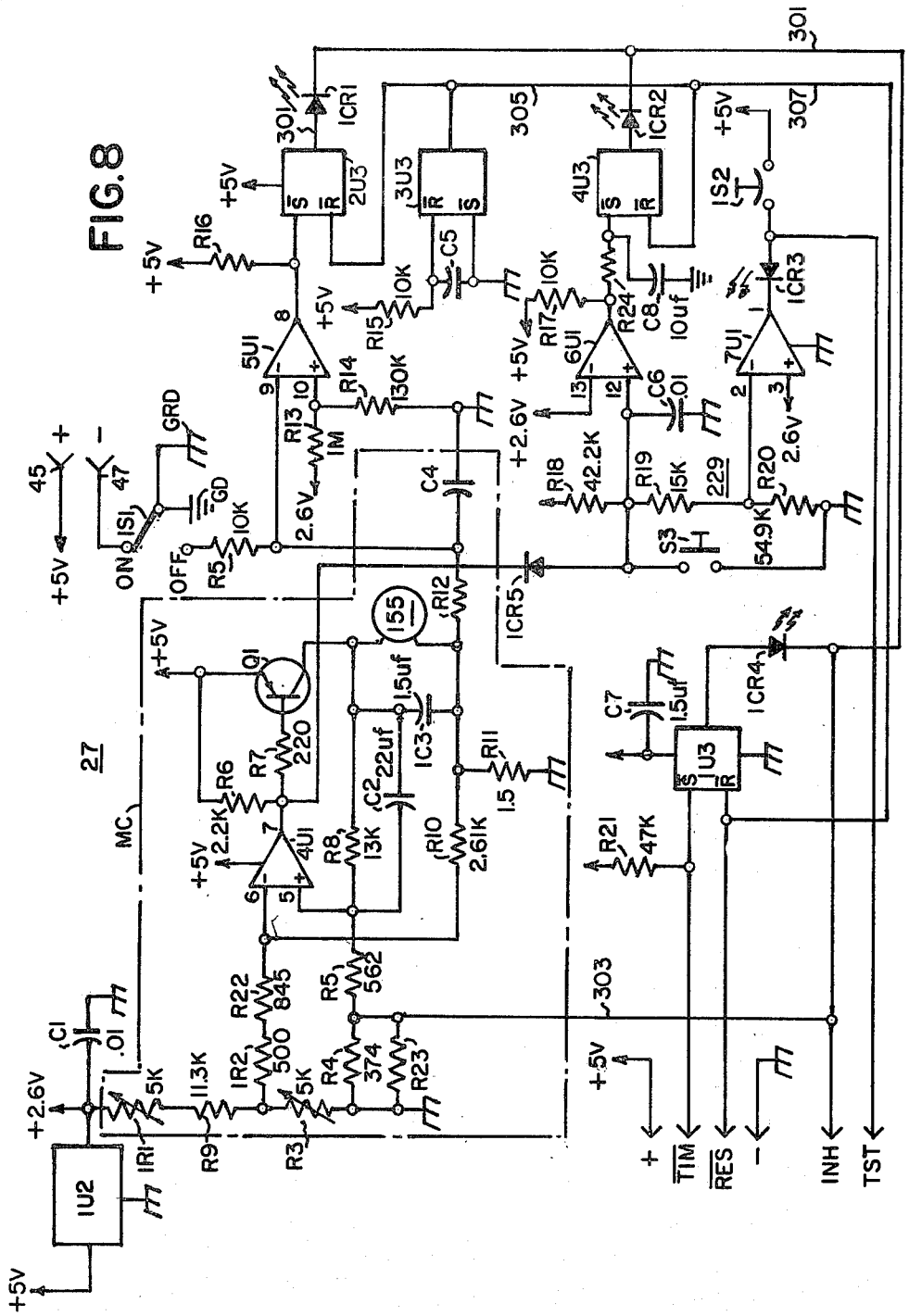
FIG. 8 is a schematic showing the control incorporated in this invention.

FIG. 8 shows the motor control MC for motor 155 near the center. The remainder of FIG. 8 shows the indicating and protective circuit. The apparatus shown in FIG. 8 includes regulator 1U2 which produces a reference voltage at its output. Typically the output is 2.6 V for any battery voltage above 4.3 volts. The 2.6 reference voltage is impressed at selected points in the circuit shown in FIG. 8.

The motor control MC responds to the loading on the motor, as the air is pumped through the pneumatic system, to maintain the flow of air; i.e., liters or milliliters per minute, constant. In this control, the motor 155 is supplied through the transistor Q1. The motor current flows in a circuit extending from the +5-volt terminal of the battery 33, through the emitter and collector of Q1, the motor, resistor R11 to ground. The current through resistor R11 is substantially equal to the motor current. The filter R12-C4 introduces a delay into the control to prevent undesired tripping of the overcurrent detector circuit for transients. The capacitor 1C3 across the motor suppresses brush noise. The apparatus is energized with switch 1S1 in the "ON" position. With 1S1 in the "OFF" position, C4 discharges to ground. Transistor Q1 is controlled by operational amplifier 4U1 whose output is connected to the base of Q1 through resistor R7. Resistor R6 between the emitter of Q1 and the output of 4U1 assures that when Q1 is to be cut off, it is completely cut off. There is a feedback network between the collector of Q1 and the positive input (pin 5) of 4U1. This network includes resistor R8 and network R4, R23, and R5. R23 is a thermister whose resistance varies exponentially with temperature; R4 linearizes the response of R23. The network R4, R23, R5 varies in resistance proportionately to change in temperature and compensates for the variation of the resistance with temperature of the copper in motor 155. Capacitor C2 introduces a delay of 0.3 sec in the response of the control to changes in the loading; i.e., the air flow. The network R8 and R4, R5 R23 set the gain of the amplifier unit 4U1-Q1.

The control for the amplifier unit is impressed on the negative input of 4U1 from the 2.6 output of 1U2 and includes the network 1R1, 1R2 R9, R22, R10, R11 and R3. The drop across R11 which measures the motor current is compared to the voltage derived through resistors 1R1, 1R2 R9, R22 and R3. R3 sets the desired air flow, 1R1 is adjusted for compensation at the high end, and 1R2 for compensation at the low end.

The circuit disclosed is able to track the changes in flow without becoming unstable. As the flow varies, the drop through R11 changes compensating for the flow change by changing the terminal voltage supplied to the motor. If the flow is increased above the set magnitude, the drop across resistor R11 decreases decreasing the terminal voltage across the motor, if the flow decreases below the set magnitude, the drop across resistor R11 increases, increasing the terminal voltage.

When the comparator in U3 signals the end of a count and there is a 0 on EQ, entered count equals preset register count, there is a 0 on T1M. Latch 1U3 is set at input S and a 1 is entered on output Q. Current flows through light-emitting diode (LED) 1CR4 and through R4 and R23 to ground. There is a 1 on plus input 5 of 1U1. Current flow through motor 155 is discontinued and the pump 93 stops pumping. The light in LED 1CR4 which is seen by the operator indicates the end of a count.

For normal operation of motor 155, the current through resistor R11 is no greater than a predetermined magnitude, typically 200 milliamperes. This magnitude is assumed for the purpose of explaining the operation of the apparatus shown in FIG. 8 in the case of excessive motor current. Based on this assumption, the voltage on pin 10 of 5U1 is about 0.3 V. If resistor R11 draws more than 200 ma., the voltage impressed on pin 9 of 5U1 through resistor R12 exceeds 0.3 volts and there is a 0 at the output of 5U1 (pin 8) and on the S input of latch 2U3. There is a 1 on the Q output of 2U3 and on conductor 301 through diode 1CR1. Diode 1CR1 is enabled indicating overcurrent. There is a 1 on conductor 303 stopping motor 155. There is also a 1 on output terminal INH, inhibit. Oscillator OSC is diabled (FIG. 7) and the counting by U3 stops. The indication as to the counts before oscillator OSC was disabled is available and provides intelligence as to how long the sampler operated before the overcurrent occurred.

Three conditions cause the output of amplifier 6U1 (pin 14) to go to 0:

1. A decrease in the voltage of battery 33 below approximately 4.3 volts. This condition is monitored by the voltage divider including the resistors R18, R19, R20. Normally these resistors impress more than 2.6 volts on pin 12 of 6U1. If the battery voltage drops below about 4.3 volts, the voltage on pin 12 drops below 2.6, the output of 6U1 goes to 0 and latch 4U3 is set. LED, 1CR2 is enabled and a 1 is impressed on conductor 301, conductor 303 and output terminal INH stopping the motor 155 and disabling the oscillator OSC.

2. IF Q1 is unable to supply sufficient current to satisfy the circuit requirements. For normal operation, the output of amplifier 4U1 (pin 7) is above 1.9 volts. Current flows through the emitter and base of Q1. The drop across diode 1CR5 is about 0.7 volts so that pin 12 of 6U1 is 2.6 volts (1.9+0.7). There is a 1 on the output of 6U1. If the voltage at the output of 4U1 is below 1.9, 1CR5 conducts, drawing pin 12 of 6U1 below 2.6 volts and there is a 1 on output Q of latch 4U3 and on conductors 301 and 303 and on output INH stopping the motor 155 and oscillator OSC.

3. On the operation of pressure switch S3. In this case, pin 12 of 6U1 goes to 0, the output goes to 1 and the motor and oscillator are stopped.

The network R24-C8 is a delay network which prevents surges from tripping latch 4U3.

Latch 3U3 operates to reset the apparatus at the start of an operation. Normally the set input S is grounded and output Q is 1. At the start of an operation when power is first applied, capacitor C5 operates as a short and R goes to 0. The latch is reset and Q goes to 0. There is a 0 on conductors 305 and 307. Latches 1U3, 2U3 and 4U3 are reset and there is also a 0 on output RES resetting the timer.

At full battery voltage, i.e., 5.3, divider R18, R19 R20 impresses a higher voltage than 2.6 on pin 2 of amplifier 7U1. The output of this amplifier goes to 0. When the test switch S2 is actuated, current flows through 1CR3 indicating that the battery is fully charged. There is also 5 volts on output TST, test. Through R8 (FIG. 7), 2½ volts is impressed on input LR of counter U3 enabling indicator U4.

While a preferred embodiment of this invention has been disclosed herein, many modifications thereof are feasible. This invention is not to be limited expect insofar as is necessitated by the spirit of the prior art.

I claim:

1. A fluid sampler including a fluid channel having an inlet branch and an outlet branch, a pump connected to said fluid channel, for conducting fluid from said inlet branch through said outlet branch, means, connected to said fluid channel, restricting the flow of fluid therethrough to a magnitude less than the capacity of said pump, whereby a pressure differential is produced in said channel across said restricting means, and a pressure regulator directly intereconnected between said inlet branch and outlet branch, responsive to said differential, for regulating the quantity of fluid delivered by said pump at said outlet to said magnitude permitted by said restricting means, said regulator including valve means operable to interconnect said inlet branch, said pump and said outlet branch in a closed circuit when the pressure difference between said outlet branch and said inlet branch exceeds said pressure differential so that, under this circumstance, the fluid in said branches is circulated by said pump in said closed circuit, and to interrupt said closed circuit when pressure difference is less than said pressure differential so that, under this latter circumstance, said fluid flows out through said outlet branch.

2. The fluid sampler of claim 1 wherein the regulator is integrated structurally with the pump.

3. The fluid sampler of claim 1 wherein the regulator includes a diaphragm, said diaphragm constituting a common wall defining a first chamber and a second chamber, means connecting said first chamber to the inlet branch, means connecting the second chamber to the outlet branch, and valve means interposed between said first and second chambers, said valve means being closed, sealing said first chamber from said second chamber, when the difference in pressure between said first chamber and said second chamber is below the pressure differential produced by the restricting means in pressure, when said difference in pressure is equal to or greater than said pressure differential whereby under this circumstance, the inlet branch, the motor and the outlet branch are connected in the closed circuit through said chambers.

4. The fluid sampler of claim 1 wherein the regulator includes a flexible diaphragm, said diaphragm constituting a common wall defining a first chamber and a second chamber, means connecting said first chamber to the inlet branch of the pump, means connecting the second chamber to the outlet branch of said pump, and valve means interposed between said first and second chambers, said valve means being closed, sealing said first chamber from said second chamber when the difference in pressure between said first chamber and said second chamber is below the pressure differential, produced by the restricting means, and being opened, by the flexing of said diaphragm, responsive to said difference in pressure, when said difference in pressure is equal to or greater than the differential in pressure produced by the restricting means.

5. The fluid sampler of claim 4 wherein the valve means includes a hollow valve seat, interposed in the diaphragm, and a pad in one of the chambers, cooperative with the seat, the said pad to be urged into engagement with said seat by the diaphragm, when the difference in pressure is below the pressure differential produced by the restricting means and to be urged out of engagement with the seat by the diaphragm when the difference in pressure is equal to or greater than said pressure differential.

6. The fluid sampler of claim 3 including means for applying force of selectable magnitude to the diaphragm for setting the difference in pressure at which the valve means opens.

7. The fluid sampler of claim 1 including means, in the conducting means, for restricting the rate of flow of fluid out of the outlet of the pump to a predetermined magnitude.

8. The fluid sampler of claim 1 including a motor for driving the pump and a control connected to said motor for controlling said motor so that the flow of fluid between the inlet branch and the outlet branch is maintained substantially constant.

9. The fluid sampler of claim 1 wherein the pressure regulator includes a first chamber, a second chamber, a flexible diaphragm interposed between said chambers as a wall common to both said chambers, a hollow valve member in said diaphragm including a valve seat, a pad in one of said chambers, cooperative with said valve member, in dependance on the differential pressure between said chambers, to engage said valve seat to seal the first chamber from the second chamber or to disengage said valve seat to connect said first and second chambers.

10. The fluid sampler of claim 9 including a spring in engagement with the membrane to exert a force on said membrane to determine the differential pressure at which the valve seats.

11. A fluid pressure regulator including a first chamber, a second chamber, a flexible diaphragm interposed between said chambers as a wall common to both said chambers, a hollow member including a valve seat in said diaphragm, a pad in one of said chambers, cooperative with said member, in dependance on the differential pressure between said chambers, to engage said valve seat to seal the first chamber from the second chamber or to disengage said valve seat to connect said first and second chambers.

12. The regulator of claim 11 wherein the flexible diaphragm is supported only around its outer rim between the first chamber and the second chamber, the said regulator including a spring in direct engagement with the diaphragm within said outer rim to exert a force on said diaphragm to determine the difference in pressure at which the valve seat passes between engagement and disengagement with the pad, and means for varying the compression of the spring to vary said force.

13. A fluid sampler including a pump having an inlet and an outlet, a flow channel, connected to said pump, for conducting fluid between said inlet and outlet as said pump operates, a flow meter in said channel, and a damper, connected to said pump and channel, to produce fluctuating flow of fluid in said channel in dephased relationship with the flow of fluid produced by said pump to smooth out the flow of fluid through said meter, said damper having a chamber at least one wall of which is composed of a flexible diaphragm, and a compression spring, interposed between said diaphragm and the opposite wall of said chamber, exerting a force tending to expand the volume of said chamber.

14. The fluid sampler of claim 13 wherein the opposite wall is also composed of a flexible diaphragm.

* * * * *